United States Patent [19]

Marschner et al.

[11] Patent Number: 5,045,307

[45] Date of Patent: Sep. 3, 1991

[54] COMPOSITION THAT PROTECTS DYED HAIR FROM FADING

[75] Inventors: Frank W. Marschner, Whitehouse Station; Frank Schebece, Edison, both of N.J.

[73] Assignee: Colgate-Palmolive Company, Piscataway, N.J.

[21] Appl. No.: 462,734

[22] Filed: Jan. 9, 1990

[51] Int. Cl.$^5$ .......................... A61K 7/06; A61K 7/42; A61K 7/44

[52] U.S. Cl. ......................... 424/59; 424/60; 424/70; 514/944

[58] Field of Search ............................. 424/70, 59, 60

[56] References Cited

U.S. PATENT DOCUMENTS

| | | | |
|---|---|---|---|
| 4,323,549 | 4/1982 | Bouillon et al. | 424/59 |
| 4,680,144 | 7/1987 | Conner | 424/60 |
| 4,837,010 | 6/1989 | Hotta et al. | 424/59 |
| 4,842,851 | 6/1989 | Grollier et al. | 424/59 |
| 4,867,964 | 9/1989 | Forestier | 424/59 |

*Primary Examiner*—Dale R. Ore
*Attorney, Agent, or Firm*—Robert Sullivan; Murray Grill; Richard Ancel

[57] ABSTRACT

A method of treating dyed hair to reduce the color loss caused by exposure to the ultraviolet rays of the sun by applying an effective amount of a hair treating formulation containing of an effective amount of a water insoluble benzophenone compound that combines readily with a hair substantive carrier composition.

6 Claims, No Drawings

COMPOSITION THAT PROTECTS DYED HAIR FROM FADING

FIELD OF THE INVENTION

The invention relates to a method of treating hair to reduce the color loss caused by the exposure to ultraviolet rays of the sun by applying an effective amount of a shampoo, rinse conditioner, hair groomer or styling gel formulation which contains 0.1–5.0% of a water insoluble benzophenone compound which combines readily with a hair substantive carrier composition, as the essential ingredient of the formulation.

SUMMARY OF THE INVENTION

The object of this invention is to provide an additive for shampoos, rinse conditioners, hair goomers, styling gels etc. to produce a formulation that reduces the color loss of dyed hair on exposure to the ultraviolet rays from the sun.

It is a further object of the invention to provide a method of treating dyed hair to prevent color loss from exposure to ultraviolet rays from the sun by applying an effective amount of a hair treating formulation that contains about 0.1–5% of a water insoluble benzophenone compound that combines readily with a hair substantive carrier composition.

BACKGROUND OF THE INVENTION

The main coloring component of hair is a dark pigment melanin, which occurs as granules embedded in the hair cortex. It is a common practice in the beauty parlor industry to treat the hair with a decolorizing agent such as peroxide and thereafter to add a dye to the hair to change color thereof. In addition the color of the hair decreases with age and it is common practice to restore the original color of the hair by applying dyes thereto.

Current rinse off hair products such as shampoos and rinse conditioners give virtually no protection against the fading of dyed hair, caused by the sun because the ultraviolet absorbers are water soluble. Commercially available shampoos containing octyl dimethyl paraaminobenzoic acid and ethylcetearyl dimonium tosylate had been found ineffective even though they are sold as shampoos that protect the hair from the ultraviolet rays from the sun.

U.S. Pat. No. 2,876,210 to Wynn discloses certain benzophenone compounds as ultraviolet absorbents. The compounds are disclosed as components perfume, aftershave lotion and lotions for applying to the skin to protect against the ultraviolet rays of the sun.

European Patent Application No. 251,398 to Sabatelli relate to chromophore containing compounds useful sunscreen agents that have the ability to absorb both UVA and UVB wavelength radiation.

The present invention provides a composition that can be added to hair treating formulations that greatly reduces the color loss in dyed hair due to exposure to the UV rays of the sun.

DETAILED DESCRIPTION OF THE INVENTION

There are numerous types of shampoos, on the highly segmented U.S. shampoo market. Among those are shampoos for normal, dry, and oily hair, types for fine, permed or damaged hair, and others that claim extra or mild cleansing. Then there are therapeutic types for dandruff, seborrhea and psoriasis control. Numerous special additives are advertised some are functional but others do not appear to be documentable. Another important segmented amount is concerned with sun damaged hair and hair color loss.

We have found that natural hair color is much more resistent to fading or change due to sunlight as simulated in a solar light simulator (Fadeometer). When it does occur it takes much longer in the environment that can be usefully simulated in the laboratory. We therefore developed a test that facilitates more rapid conditions to make relative comparisons and evaluations.

We found that hair colorant when added to natural wool swatches gave satisfactory results in a laboratory color fading test. A test was developed which exposes dyed wool challis swatches treated with UV absorbers or washed with shampoo etc using a fadeometer to check on the percentage of color loss. Wool was selected because it nearly resembles the protein composition of human hair.

Our investigation was carried out in three phases. In the first phase ultraviolet absorbers were screened and benzophenone 2 was selected as the most desirable additive for shampoo. In the second phase of our investigation the hair substantive carrier compositions were investigated. The third phase of our investigation relates to prior formulations. In addition to shampoo, creme rinse conditioners, liquid hair groomers and styling gels were formulated.

The wool swatch method was used in our evaluations. This method measures the percent reduction of color fading for ultraviolet absorbers in products containing them such as shampoos, conditioners, hair dressing and other products which can be sprayed, thinly applied or washed onto the wool swatches. The wool swatches having a dimension of 3"×9" are coloring applied according to the package directions. The dye sold under the tradename Performing Preference by Loreal (Fancoises Sunset Flame Permanent Dye) was used in each of the tests. The swatches were taped onto a smooth vertically held board of plexiglass. A piece of non-penetreatable material such as a metal plate or cardboard is placed over the areas that are not to be exposed. An area approximately 2½" long was sprayed to saturation with an ultraviolet absorber solution. The swatches were hung to dry and initial Rd, a, b color values were taken using a Gardner Reflectometer.

The sunscreen solution was prepared by dissolving 1 gram of the ultraviolet absorber in 99 grams of SD40 alcohol. The solution was placed in a spray bottle for application to the swatches. In case of product evaluation the area used for the evaluation was washed carefully and rinsed twice with shampoo or once with conditioner. The swatches are normally cut into two portions and an area contained the conditioner washed separately dried and then the swatches are rejoined. The products other than shampoos such as leave on liquid products can be applied lightly with a brush.

In exposing the swatches to a Fadeometer the swatches are secured to a revolving frame of the Fadeometer, using a single swatch holder and are attached to a wire mesh screen wire with clips. The unexposed area is covered on both sides with aluminum foil. The exposed but untreated area, the diffusion area and the treated areas are exposed to 16 hours of ultraviolet rays in the Fadeometer. The total reflectance values from the areas are retaken after exposure.

Rd (total reflectance) and a and b color values are calculated separately. The total reflectance values change and are the primary basis for determining percentage reduction in color fading. "a" and "b" color values seldom change, so before and after total reflectance values were used and averaged. The total reflectance values are obtained for the untreated and treated area by subtracting before and after total reflectant values. The percent reduction in color fading is calculated using the following formula. Theoretical percent reduction in color fading $$= \frac{Rd\ B - Rd\ D}{\text{average } Rd \text{ control}} \times 100$$

To simplify the calculation the total reflectance is designated by Rd the Exposed untreated area is designated B, Exposed treated area is designated D. Our invention is illustrated by the following specific but not limiting Examples.

EXAMPLE I

Several sunscreen compositions were evaluated in Phase One. The results of this evaluation is set out in Table I and II below.

TABLE I

| 1% UV Absorber Solution | % Reduction in Fading |
|---|---|
| Benzophenone 9 | 9.7 |
| Benzophenone 11 | 7.2 |
| Benzophenone 1 | 6.2 |
| Benzophenone 8 | 4.5 |
| 50/50 Octyl Methoxycinnamate: Benzophenone 4 | 4.5 |
| Benzophenone 12 | 4.5 |
| Benzophenone 4 | 4.1 |
| Ethyl Dihydroxypropyl PABA | 2.1 |
| Octyl Methoxycinnamate | 2.1 |
| Benzophenone 3 | 1.7 |
| Octyl Dimethyl PABA | 0 |
| 50/50 Dimethyl PABA Ethyl Cetearyl Dimonium Tosylate:Octyl Methoxycinnamate | 0 |
| 50/50 Dimethyl PABA Ethyl Cetearyl Dimonium Tosylate (1): Octyl Dimethyl PABA | 0 |

TABLE II

| 1% UV Absorber Solution | % Reduction in Fading |
|---|---|
| Benzophenone 2 | 8.4 |
| Benzophenone 11 | 8.4 |
| 50:50 Benzophenone 11/Butyl Methoxy Dibenzoyl Methane | 8.3 |
| 50:50 Benzophenone 11/Octyl Dimethyl PABA | 7.8 |
| 50:50 Benzophenone 8/Octyl Dimethyl PABA | 6.8 |
| Octrizole | 4.2 |
| Butyl Methoxy Dibenzoyl Methane | 3.5 |
| TEA Salicylate | 3.0 |
| Octyl Methoxycinnamate | 1.7 |
| Tri PABA Panthenol | 1.7 |
| Methyl Anthranilate | 1.1 |
| Octyl Salicylate | 1.0 |
| Benzophenone 12 | 0.7 |
| Octyl Dimethyl PABA | 0.7 |
| Benzophenone 3 | 0 |

Benzophenone 9 - Na 2, 2' dihydroxy-4-4' dimethoxy-5-sulfobenzophenone
Benzophenone 11-2,4-dihydroxy benzophenone
Benzophenone 2- 2, 2' 4, 4' tetrahydroxybenzophenone PABA paraamino benzoic acid
(1) A commercially available sunscreen agent It is apparent from the data presented in Tables I and II that benzophenone 2, 9 and 11 provide the best dye color protection. Benzophenone 11 was not considered for the inclusion in the formulations in the second phase of our investigation because it is water soluble. Although benzophenone 9 would obviously have satisfactory results. It was not used in our evaluation because it is difficult to solubilize in alcohol or in the hair substantive carrier compositions. In addition both benzophenones 9 and benzophenone 11 are undesirably yellow in color. Benzophenone 2 was used in the subsequent evaluations because it is acceptable in color, readily soluble in alcohol and in most of the hair substantive carrier compositions. It should be noted that the commercially available sunscreen agent did not reduce the fading in the test.

EXAMPLE II

Four shampoo formulations were prepared. In preparing the formulations part 2 was initially prepared by dissolving the benzophenone in alcohol. The carrier, Miristocor was added and mixed until the solution was clear. Water was then added to the mixture to form an emulsion. In the second step of the preparation Betaine was mixed in, followed by the water from part one. In the third step of the preparation the sodium laureth sulfate was added and mixed to prepare a clear solution. The ingredients of part 5 were added in the final step of preparation of the formulation in the order set out in the table. The formulation was mixed throughly and a clear viscous shampoo was formed. The components of the formulations are set out in table III.

TABLE III

| | Formula Code | | | |
|---|---|---|---|---|
| | "Z" % | "K" % | "G" % | "U" % |
| Part 1 | | | | |
| Water | 37.607 | 37.607 | 37.607 | 37.607 |
| Part 2 | | | | |
| SD40 Ethanol (95%) | 1.000 | 1.000 | 1.000 | 1.000 |
| Benzophenone 2(1) | 0.500 | 0.500 | 0.500 | 0.500 |
| Miristocor(2) | 2.5 | — | — | — |
| Naltex EF(3) | — | 2.5 | — | 2.500 |
| Cerephyl 65(4) | — | — | 2.5 | — |
| Octyl Methoxycinnamate(5) | — | — | — | 0.500 |
| Water | 5.000 | 5.000 | 5.000 | 5.000 |
| Part 3 | | | | |
| Cocoamidopropyl Betaine (30%) | 10.000 | 10.000 | 10.000 | 10.000 |
| Part 4 | | | | |
| Sodium Laureth (2EO) Sulfate (27%) | 40.714 | 40.714 | 40.714 | 40.714 |
| Part 5 | | | | |
| Formalin | 0.123 | 0.123 | 0.123 | 0.123 |
| Na4EDTA (50% Solution) | 0.156 | 0.156 | 0.156 | 0.156 |
| Perfume | 0.400 | 0.400 | 0.400 | 0.400 |
| Water | 2.000 | 2.000 | 2.000 | 2.000 |
| | 100.000 | 100.000 | 100.000 | 100.000 |

(1)UVINUL D50
(2)Myristamidopropyl Dimethylamine Phosphate
(3)Oleyl Dimethylaminopropylamido Ethonium Ethosulfate
(4)Quaternium 26
(5)Parsol MCX

EXAMPLE III

The carriers used in the formulations set out in Example II were cationic. A formulation was prepared that contains a mixture of cationic and anionic carriers. The formulation was prepared using the general techniques as supplied in example II. The formulation designated shampoo O in Table IV below.

TABLE IV

| Shampoo "O" | |
|---|---|
| | % |
| Part 1 | |
| Water | 48.225 |
| Polymer LR-30M[1] | 0.300 |
| Part 2 | |
| Pationic RSL[2] | 1.000 |
| Lexein QX 3000[3] | 1.500 |
| SD40 Ethanol (95%) | 1.000 |
| Benzophenone 2 | 0.500 |
| Cocoamidopropyl Betaine (30%) | 4.400 |
| Sodium Hydroxide (10% Soln.) | 0.100 |
| Water | 8.000 |
| Part 3 | |
| Sodium Laureth 2 EO Sulfate (27%) | 32.900 |
| Part 4 | |
| Cremophor RH 40[4] | 0.500 |
| Perfume | 0.500 |
| Kathon CG Preservative | 0.075 |
| Sodium Chloride | 1.000 |
| | 100.000 |

[1]Polyquaternium 10
[2]Sodium isostearoyl Lactylate
[3]Cocotrimonium collagen Hydrolysate
[4]PEG 40 Hydrogenated Castor Oil

EXAMPLE IV

The shampoos designated "Z", "O", "K", "G", and "U" in tables II and IV were evaluated using wool swatches in the method described above. The percentage reduction in fading for each of these formulations are listed out in Table V;

TABLE V

| Shampoos | % Reduction in Fading |
|---|---|
| Control Benzophenone 2 (1% in SD 40 Ethanol) | 6.1 |
| "Z" | 4.6 |
| "O" | 4.0 |
| "K" | 3.4 |
| "G" | 3.4 |
| "U" | 3.3 |
| Commercial available formulation | 0 |

It is apparent from the data that each of the shampoos give satisfactory results. The results are generally comparable. It should be noted that no reduction in fading resulted when the commercially available formulation was used.

It is obvious that the addition of benzophenone 2 to shampoo formulations greatly improves their ability to reduce fading of dyed hair.

EXAMPLE V

Shampoo formulations were prepared using different carrier compositions, all of the carrier compositions prepared in the this series of runs were cationic. The composition of these formulations set out in table VI;

TABLE VI

| Shampoos with Benzophenone 2 and Cationics | | | | |
|---|---|---|---|---|
| Shampoo | A | C | D | E |
| SD40 Alcohol | 1.0 | 1.0 | 1.0 | 1.0 |
| Uvinul D50[1] | 0.5 | 0.5 | 0.5 | 0.5 |
| Miristocor[2] | 2.5 | | | |
| Pationic ISL[3] | | | | |
| Lexein QX 3000[4] | | | | |
| Merquat 550[5] | | | 2.5 | |
| Naltex EF[6] | | 2.5 | | 1.5 |
| Cerephyl 65[7] | | | | 1.0 |
| Water Part 1 | 5.0 | 5.0 | 5.0 | 5.0 |
| Tegobetaine L7 | 10.0 | 10.0 | 10.0 | 10.0 |
| Polymer LR-30M | | | | |
| Water (Part 2) | 39.607 | 39.607 | 39.107 | 39.607 |
| Sodium Lauryl Ether (2EO) Sulfate (28%) | 40.714 | 40.714 | 40.714 | 40.714 |
| Cremophor RH 40 Fidelio Perfume | 0.4 | 0.4 | 0.4 | 0.4 |
| Kathon CG | | | | |
| Sodium Chloride | | | 0.5 | |
| Formalin | 0.123 | 0.123 | 0.123 | 0.123 |
| Na₄EDTA (50% Soln) | 0.156 | 0.156 | 0.156 | 0.156 |
| | 100.00 | 100.00 | 100.00 | 100.00 |

[1]Benzophenone 2
[2]Myristamidopropyl Dimethylamine Phosphate 75%
[3]Sodium Isostearoyl Lactylate
[4]Cocotrimonium Collagen Hydrolysate
[5]Polyquaternium 7 (acrylamide copolymer 8%)
[6]Oleyl Dimethylaminopropyl amidoethonium ethosulfate
[7]Mink amidopropyl Dimethyl 2- Hydroxyethyl ammonium chloride The formulations were prepared using the general techniques described in example II.

EXAMPLE VII

In this example a formulation designated shampoo B was prepared. This formulation differs from the other formulations in that it contains a polymer. The formulation was prepared by mixing the polymer in cold water in a mixing vessel. The mixture was heated to 140° F. that dissolved the polymer. A mixture containing the benzophenone 2 in alcohol was prepared separately and an anionic cocarrier (Pationic) was added. The sodium hydroxide and cationic carrier (Lexein) was added. The Betaine and water were then added and the mixture was heated to dissolve all the constituents. In the next step of the process the cationic mixture was added to the polymer solution. The sodium lauryl ether sulfate was then added to the mixture. The other components were then added. The product was cooled to 77° F. and the viscosity adjusted to 1500±500 CPS with sodium chloride. A clear shampoo product was formed. The composition of the formulation is set out in Table VII:

TABLE VII

| Shampoo | B |
|---|---|
| SD40 Alcohol | 1.0 |
| Uvinul D50[1] | 0.5 |
| Miristocor[2] | |
| Pationic ISL[3] | 1.0 |
| Lexein QX 3000[4] | 1.5 |
| Merquat 550[5] | |
| Naltex EF[6] | |
| Cerephyl 65[7] | |
| NaOH (10% Soln) | 0.1 |
| Water Part 1 | 8.0 |
| Tegobetaine L7 | 4.4 |
| Polymer LR-30M | 0.3 |
| Water (Part 2) | 48.725 |
| Sodium Lauryl Ether (2EO) Sulfate (28%) | 32.9 |
| Cremophor RH 40 Perfume | 0.500 |
| Kathon CG | 0.075 |
| Sodium Chloride | 1.000 |
| Formalin | |
| Na₄EDTA (50% soln) | |
| | 100.00 |

EXAMPLE VIII

The shampoos designated A, B, C. D. and E were evaluated using techniques described above. The results are set out in table VIII

TABLE VIII

|  | % Reduction in Fading |
|---|---|
| Straight Benzophenone 2 (1% Soln Control) | 6.1 |
| Shampoo A | 4.6 |
| Shampoo B | 4.1 |
| Shampoo C | 3.4 |
| Shampoo D | 3.0 |
| Shampoo E | 2.6 |
| Commercially available sunscreen shampoo | 0.4 |

It is apparent from the data presented in table VIII the shampoo designated A, B, C, D, and E had considerable better sun screen properties than the commercially available suncreen shampoo.

EXAMPLE IX

A series of runs were completed to determine the optimum concentration of Benzophenone 2 in two best shampoos. The level of benzophenone 2 in the shampoo was varied from 0.25–1%. The shampoo designated A, B were used for this evaluation. Shampoos were compared with the commercially available sunscreen shampoo. The results are set out in table IX:

TABLE IX

Formula Optimization/Color Fading Test Results

| Shampoo | % Benzophenone 2 | % Reduction in Fading |
|---|---|---|
| Straight Benzophenone 2 (1% Soln Control) |  | 10.3 |
| A | 0.75 | 6.0 |
| A | 0.50 | 3.6 |
| A | 0.25 | 3.6 |
| A | 1.0 | 3.4 |
| B | 1.0 | 5.7 |
| B | 0.75 | 5.4 |
| B | 0.50 | 4.5 |
| B | 0.25 | 3.2 |
| B w/o polymer | 0.25 | 1.4 |
| Commercially available sunscreen shampoo |  | 0.3 |

Reduction in the Benzophenone-2 level invariably resulted in relatively lower ultraviolet protection except in the case of shampoo A with 1% Benzophenone-2. Maximum reduction in color fading achieved 0.75 Benzophenone-2 in shampoo A and 1% Benzophenone-2 in Shampoo B. All the shampoos outperformed the commercially available sunscreen shampoo.

EXAMPLE X

A series of runs were completed in which liquid hair groomer, creme rinse conditioner and styling gel formulation are prepared containing benzophenone-2.

In this example a liquid hair groomer was prepared by dissolving the benzophenone-2 in alcohol and polyalkylene glycol. This solution was then mixed with a solution containing the water, polyvinylpyrolidone and glycerin in the second step. In the third step of the process the perfume and hydrogenated castor oil were combined into the formulation. The formulation is set out in Table X below:

TABLE X

Liquid Hair Groomer

|  | % |
|---|---|
| Part 1 |  |
| SD40 Alcohol | 20.0 |
| Benzophenone 2 | 0.5 |
| Ucon 50HB 660[1] | 15.0 |
| Part 2 |  |
| Water | 60.1 |
| PVP/K90[2] | 1.0 |
| POE 26 Glycerine | 3.0 |
| Part 3 |  |
| Cremophor RH40[3] | 0.3 |
| Perfume | 0.1 |
|  | 100.00 |

[1] Polyalkylene Glycol
[2] Polyvinylpyrrolidone
[3] PEG 40 Hydrogenated Castor oil

EXAMPLE XI

A creme rinse conditioner was prepared by dissolving citric acid and cetyl trimethylammonium chloride in water and the mixture was heated to 80–85° C. Mineral oil and cetyl alcohol were heated to 80–85° C. in a separate vessel and the benzophenone 2 was added to this mixture. The two mixtures were combined and cooled to 39° C. The perfume and formalin were then added and a thick opaque product resulted. The formulation is set out in Table XI:

TABLE XI

Cream Rinse Conditioner

|  | % |
|---|---|
| Part 1 |  |
| Water | 47.32 |
| Citric Acid | 0.10 |
| CTAC (25% Soln)[1] | 2.00 |
| Part 2 |  |
| Heavy Mineral Oil | 0.65 |
| Cetyl Alcohol | 3.50 |
| Propylene Glycol | 0.50 |
| Benzophenone 2 | 0.30 |
| Part 3 |  |
| Water | 45.33 |
| Part 4 |  |
| Formalin | 0.10 |
| Perfume | 0.20 |
|  | 100.00 |

[1] Cetyl Trimethylammoniumchloride

EXAMPLE XII

In this example the styling gels were prepared designated styling gels 1 and 2. The components were separated into four parts. Part 1 was prepared by dissolving the polymer in water and heating. The EDTA and Glycerin were added and combined with the polyethyleneglycol. The polyvinylpyrrolidone was dissolved in alcohol in a separate vessel. The Benzophenone 2, the oleyl ether, and the salicylate were then added. Parts 1 and 2 were combined by rapid mixing. Part 3 was prepared by dissolving the perfume in the PEG 40 Hydrogenated castor oil and this mixture was added to parts 1 and 2. The preservative was then added and a cloudy gel was recovered.

These formulation are set out in Table XII below:

TABLE XII

| | Styling Gels | |
|---|---|---|
| | #1 % | #2 % |
| Part 1 | | |
| Water | 82.000 | 83.01 |
| Carbomer 940[1] | 0.40 | 0.40 |
| Na₄EDTA | 0.05 | 0.04 |
| Glycerine | 2.00 | |
| Ucon 50 HB 660[6] | 1.75 | 1.75 |
| Part 2 | | |
| SD40 Alcohol | 10.00 | |
| PVP/K30[2] | 2.00 | 2.00 |
| Volpo 10[3] | 0.50 | 0.50 |
| TEA Salicylate[4] | | 1.00 |
| Benzophenone 2 | 0.20 | 0.20 |
| Triethanolamine | 0.60 | 0.60 |
| Part 3 | | |
| Cremophor RH 40[7] | 0.3 | 0.30 |
| Perfume | 0.1 | 0.10 |
| Part 4 | | |
| Glydant[5] | 0.1 | 0.10 |
| | 100.00 | 100.00 |
| | | Note Line up |

[1]Carbopol 940 Ammonium Carboxyvinyl polymer
[2]Polyvinylpyrrolidone
[3]Oleth-10 oleyl ether
[4]Sunarome W
[5]DMDM Hydantoin
[6]Polyalkylene glycol
[7]PEG 40 Hydrogenated castor oil

EXAMPLE XIII

The formulation set out in Table X, XI and XII were checked using the techniques described in example II above. The results are set out in Table XIII.

TABLE XIII

| Application to Products Other Than Shampoos | |
|---|---|
| | % Reduction in Fading |
| Styling Gel #2 | 6.5 |
| Hair Groomer | 5.7 |
| Cream Rinse Conditioner | 4.7 |
| Styling Gel #1 | 3.1 |
| Commercially available Mousse | 3.6 |

The results above will show that benzophenone 2 is effective in rinse conditioners, and hair grooming aids, product efficacy can be improved with the supplemental addition of other ultraviolet absorbers as the salicylate as shown in the results of the test of styling gel 2.

Benzophenone 2 is demonstrated to be efficaceous in shampoos and other products such as rinse conditioners, hair groomer and styling gels. A combination of 1% Triethanolamine Salicylate and 0.2% benzophenone showed encouraging results in styling gel two. Other compounds with benzophenone-2 would be expected to give similar or improved results.

Obviously many modifications and variations of the invention may be made without departing from the essence and scope thereof, only such limitations should be applied as are indicated in the appended claims.

What is claimed is:

1. A method of treating dyed hair to reduce color loss caused by exposure to the ultraviolet rays of the sun consisting essentially of applying an effective amount of a hair treating composition selected from the group consisting of shampoos, liquid groomers, styling gels and cream rinses containing from about 0.1 to 5 percent benzophenone compound selected from the group 2,2',4,4' tetrahydroxybenzophenone and 2,4 dihydroxy benzophenone and 1 to 5 percent of a hair substantive carrier composition.

2. The method according to claim 1 wherein the carrier composition is a mixture of cocotrimonium collagen hydrolysate and isostearoyl lactylate.

3. The method according to claim 1 wherein the hair treating formulation additionally contains about 1 percent ethyl alcohol, myristamidopropyl dimethyl amine phosphate, betaine, perfume and water.

4. The method according to claim 1 wherein the hair treating composition is a shampoo consisting essentially of 45 to 85 percent water, 0.1 to 5 percent 2,2',4,4', tetrahydroxybenzophenone, 8 to 20 percent sodium laureth sulfate, 1 to 5 percent betaine in admixture with about 0.5 percent perfume and 0.1 to 1 percent E.D.-T.A.

5. The method according to claim 1 wherein the hair treating composition is a liquid hair groomer consisting essentially of about 60 percent water, about 0.5 percent 2,2',4,4' tetrahydroxybenzophenone, about 15 percent polyalkylene glycol, about 20 percent alcohol, about 1 percent polyvinylpyrrolidone, about 3 percent glycerine, about 0.3 percent hydrogenated castor oil and about 0.1 percent perfume.

6. The method according to claim 1 wherein the hair treating composition is a cream rinse conditioner consisting essentially of about 92 percent water, about 3.5 percent cetyl alcohol, about 2 percent cetyl trimethylammonium chloride, about 0.65 percent heavy mineral oil, about 0.5 percent propylene glycol, about 0.3 percent 2,2',4,4' tetrahydroxybenzophenone and about 0.1 percent formalin.

* * * * *